(12) United States Patent
Yelin

(10) Patent No.: US 8,780,176 B2
(45) Date of Patent: Jul. 15, 2014

(54) VESSEL IMAGING SYSTEM AND METHOD

(75) Inventor: Dvir Yelin, Haifa (IL)

(73) Assignee: Technion Research & Development Foundation Limited, Haifa (IL)

( * ) Notice: Subject to any disclaimer, the term of this patent is extended or adjusted under 35 U.S.C. 154(b) by 341 days.

(21) Appl. No.: 12/461,558

(22) Filed: Aug. 17, 2009

(65) Prior Publication Data

US 2010/0045778 A1  Feb. 25, 2010

Related U.S. Application Data

(60) Provisional application No. 61/089,132, filed on Aug. 15, 2008.

(51) Int. Cl.
*H04N 13/00* (2006.01)
*A61B 1/04* (2006.01)
*H04N 15/00* (2006.01)

(52) U.S. Cl.
USPC ............. 348/45; 348/42; 348/46; 600/478; 600/504

(58) Field of Classification Search
USPC .............. 348/42, 45, 46; 600/504, 478
See application file for complete search history.

(56) References Cited

U.S. PATENT DOCUMENTS

| | | | | |
|---|---|---|---|---|
| 5,371,368 A | * | 12/1994 | Alfano et al. | 250/341.1 |
| 6,554,775 B1 | * | 4/2003 | Peyman et al. | 600/504 |
| 6,621,917 B1 | * | 9/2003 | Vilser | 382/128 |
| 7,904,138 B2 | | 3/2011 | Goldman et al. | |
| 2006/0142662 A1 | | 6/2006 | Van Beek | |
| 2007/0188855 A1 | | 8/2007 | Shishkov et al. | |
| 2008/0021329 A1 | | 1/2008 | Wood et al. | |
| 2008/0045817 A1 | | 2/2008 | Van Beek et al. | |
| 2008/0097225 A1 | * | 4/2008 | Tearney et al. | 600/478 |
| 2010/0045778 A1 | | 2/2010 | Yelin | |

FOREIGN PATENT DOCUMENTS

| | | | |
|---|---|---|---|
| JP | 2007127860 A | * | 5/2007 |
| WO | WO 2008/005282 | | 1/2008 |
| WO | WO 2009/037432 | | 3/2009 |
| WO | WO 2013/108209 | | 7/2013 |

OTHER PUBLICATIONS

Motz et al., "Spectral- and Frequency-Encoded Fluorescence Imaging", Optics Letters, XP001235409, 30(20): 2760-2762, Oct. 15, 2005. p. 2760, 1-h Col., § 2-p. 2762, 1-h Col., § 1.*

Partial European Search Report and the European Search Opinion Dated Jan. 13, 2010 From the European Patent Office Re.: Application No. 09010571.9.

Motz et al. "Spectral- and Frequency-Encoded Fluorescence Imaging", Optics Letters, XP001235409, 30(20): 2760-2762, Oct. 15, 2005. p. 2760, 1-h Col., § 2-p.2 762, 1-h Col., § 1.

(Continued)

*Primary Examiner* — Liangche A Wang

(57) ABSTRACT

A system and a method for acquiring an image of a particle flowing in a vessel, the system comprising a light source for generating an illuminating light, an imaging probe for laterally statically illuminating at least a portion of said vessel with the illuminating light, a detection unit for detecting emitted light from an illuminated portion of said particle, and a processor unit for reproducing an image of the illuminated portion of said particle from the emitted light.

49 Claims, 8 Drawing Sheets

(56) References Cited

OTHER PUBLICATIONS

Yelin et al. "Three-Dimensional Miniature Endoscopy.A Single Optical Fibre Acts as a Flexible Probe to Transmit a Superior Image of an Internal Landscape", Nature, XP002558589, 443(7113): 765, Oct. 19, 2006.

Response Dated Mar. 15, 2011 to Communication Pursuant to Article 94(3) EPC of Sep. 17, 2010 From the European Patent Office Re. Application No. 09010571.9.

Communication Pursuant to Article 94(3) EPC Dated Sep. 17, 2010 From the European Patent Office Re. Application No. 09010571.9.

Golan et al. "Flow Cytometry Using Spectrally Encoded Confocal Microscopy", Optics Letters, 35(13): 2218-2220, Jul. 1, 2010.

Yelin et al. "Volumetric Sub-Surface Imaging Usding Spectrally Encoded Endoscopy", Optics Express, 16(3): 1748-1757, Feb. 4, 2008.

Bishop et al. "Effect of Erythrocyte Aggregation on Velocity Profiles in Venules", American Journal of Physiology, Heart and Circulatory Physiology, 280(1): H222-H236, Jan. 2001.

Golan et al. "High-Speed Interferometric Spectrally Encoded Flow Cytometry", Optics Letters, 37(24): 5154-5156, Dec. 15, 2012.

Konstantinopoulos et al. "Venous Levels of Shear Support Neutrophil-Platelet Adhesion and Neutrophil Aggregation in Blood Via P-Selection and Beta2-Integrin", Circulation, 98: 873-882, Nov. 1, 1998.

Schmid-Schoenbein et al. "The Interaction of Leukocytes and Erythrocytes in Capillary and Postcapillary Vessels", Microvascular Research, 19: 45-70, 1980.

International search Report and the Written Opinion Dated May 28, 2013 From the International Searching Authority Re. Application No. PCT/IB2013/050442.

Hoffbrand et al. "Erythropoiesis and General Aspects of Anaemia". "The White Cells 1: Granulocytes, Monocytes and Their Benign Disorders", Essential Haematology, Chap.2 and 7: 18 and 94, 1980 ff.

\* cited by examiner

Cross-sectional imaging: size, shape, location, many particles

Single measurement: event, signal, single particle

VESSEL IMAGING SYSTEM AND METHOD

RELATED APPLICATIONS

This application claims the benefit of U.S. Provisional Patent Application No. 61/089,132, filed on Aug. 15, 2008, the disclosure of which is incorporated herein by reference in its entirety.

FIELD AND BACKGROUND OF THE INVENTION

The present invention, in some embodiments thereof, relates to imaging devices and, more particularly, but not exclusively, to imaging systems and methods for medical and scientific applications.

Endoscopic confocal microscopy devices are extensively used in minimally invasive medical diagnosis to look below tissue surfaces and for intervention purposes. Confocal microscopy is a technique generally used to acquire an image of a specimen and is based on focusing illuminating light from a point source to a point on the specimen, and focusing emitted light (responsive to the illuminating light) from the illuminated point on the specimen unto a small pinhole in an opaque screen. As only the emitted light from the illuminated point is focused unto the hole, the emitted light passes through the pinhole while all other light not emitted by the point is substantially blocked out. A detector on the other side of the screen detects the amount of emitted light passing through the pinhole and quantifies the amount for image reproduction purposes. As only one point in the specimen is illuminated at a time, two-dimensional (2D) or three-dimensional (3D) imaging generally is done by scanning over a regular raster (a rectangular pattern of parallel scanning lines) in the specimen.

A technique generally used to integrate confocal microscopy inside probes used in medical and scientific applications such as, for example, endoscopic probes and catheters, is spectrally encoded confocal microscopy (SECM). In SECM, the specimen is generally scanned line by line, with illuminating light at a different wavelength hitting each point along a line (each point on a line is "encoded" by a different wavelength). Emitted light from each point (each point emitting light at a different wavelength) is detected by a detector and, spatial information of the specimen along the line may be decoded by measuring the detected wavelengths. A 2D image may be reproduced by relatively slowly scanning the encoded lines mechanically within the probe.

An alternative technique to SECM is spectrally encoded endoscopy (SEE). SEE described in "Volumetric sub-surface imaging using spectrally encoded endoscopy", by D. Yelin et al, Optics Express 1750/Vol. 16, No. 3/4 Feb. 2008; as follows: "Spectrally encoded endoscopy (SEE) [7] is a recently developed technique that utilizes wavelength to encode transverse image information. The SEE probe, comprising a single optical fiber, a diffraction grating, and a low NA lens, focuses spectrally dispersed light onto the sample. In turn, each point along this line is illuminated by a distinct spectral band. Each line of the image is acquired by measuring the spectrum of light reflected from the sample and returned back through the SEE probe using a high-speed spectrometer that resides outside the body. The second dimension of the image is obtained by moving the fiber at slow rates (e.g. 30 Hz). Without the need for rapid transverse scanning at the distal end of the endoscope, SEE allows video rate imaging to be performed through a miniature (i.e. 350 µm diameter) endoscopic device [13]. When the SEE probe is placed in the sample arm of an interferometer, it additionally can achieve three-dimensional topological, surface imaging in real-time, by use of time [14] and spectral [13, 15] domain low coherence interferometry."

SUMMARY OF THE INVENTION

According to an aspect of some embodiments of the present invention there is provided a method for acquiring an image of a particle flowing in a vessel, the method comprising laterally statically illuminating at least a portion of the vessel with an illuminating light, detecting emitted light from an illuminated portion of the particle, and reproducing an image of the illuminated portion of the particle from the emitted light. Optionally, the image of the illuminated portion of the particle is a two-dimensional (2D) image. Optionally, detecting light from the illuminated portion of the particle comprises measuring a spectrum of the emitted light. Optionally, detecting emitted light comprises detecting fluorescence, second harmonic generation, third harmonic generation, luminescence, Coherent anti-Stokes Raman scattering, Raman scattering, multi-photon fluorescence, or phosphorescence, or any combination thereof. Optionally, the method comprises confocal gating of the emitted light.

According to some embodiments of the invention, the method further comprises acquiring an image of a cross-section of the portion of the vessel. Optionally, the image of the cross-section of the vessel comprises a cross-section of one or more particles in the portion of the vessel.

According to some embodiments of the invention, the method further comprises spectrally dispersing the illuminating light along an axis. Optionally, the method further comprises collimating the illuminating light prior to spectrally dispersing the light.

According to some embodiments of the invention, the method further comprises creating interference between the emitted light and a reference light to determine axial location of the illuminated portion of said particle. Optionally, the method comprises reproducing a three-dimensional (3-D) image of the illuminated portion of the particle.

According to some embodiments of the invention, the method comprises creating interference between the emitted light and a reference light to determine an axial component of a speed of the particle in the vessel.

According to some embodiments of the invention, the method comprises sending the illuminating light through a single mode optical fiber. Optionally, the method comprises sending the illuminating light through a multi-mode optical fiber. Optionally, the method comprises receiving the emitted light through a single mode optical fiber. Optionally, the method comprises receiving the emitted light through a multi-mode optical fiber.

According to some embodiments of the invention, the method comprises varying the wavelength of the illuminating light. Optionally, the illuminating light is a broad bandwidth light.

According to some embodiments of the invention, the method comprises counting a number of particles in the vessel. Optionally, the method comprises determining a location, a speed of flow, a size, a length, a shape, a color, or a brightness of a particle, or any combination thereof, in the vessel.

According to some embodiments of the invention, the method further comprises acquiring the image of the particle in-vivo. Optionally, the method comprises acquiring the image of the particle ex-vivo (outside the body).

According to an aspect of some embodiments of the present invention there is provided a system for acquiring an image of a particle flowing in a vessel, the system comprising a light source for generating an illuminating light, an imaging probe for laterally statically illuminating at least a portion of the vessel with the illuminating light, a detection unit for detecting emitted light from an illuminated portion of the particle, and a processor unit for reproducing an image of the illuminated portion of the particle from the emitted light. Optionally, the image of the illuminated portion of said particle is a two-dimensional (2D) image. Optionally, the detection unit detects fluorescence, second harmonic generation, third harmonic generation, luminescence, Coherent anti-Stokes Raman scattering, Raman scattering, multi-photon fluorescence, or phosphorescence, or any combination thereof. Optionally, the imaging probe includes confocal gating of the emitted light.

According to some embodiments of the invention, the imaging probe captures the emitted light from the illuminated portion of the particle. Optionally, the imaging probe is an endoscope. Optionally, the imaging probe is a catheter. Optionally, the imaging probe illuminates a portion of the particle in-vivo. Additionally or alternatively, the imaging probe illuminates a portion of the particle ex-vivo (outside of the body).

According to some embodiments of the invention, the processor unit reproduces an image of a cross-section of the portion of the vessel. Optionally, the image of the cross-section of the portion of the vessel comprises a cross-section of one or more particles in the portion of the vessel. Additionally or alternatively, the processor unit counts a number of particles in the vessel. Optionally, the processor unit determines a location, a speed of flow, a size, a length, a shape, a color, or a brightness of a particle, or any combination thereof, in the vessel.

According to some embodiments of the invention, the detection unit comprises a spectrometer for measuring a spectrum of the emitted light. Optionally, the detection unit comprises a camera for capturing a single shot of the emitted light. Optionally, the detection unit comprises a single detector for measuring a wavelength of the emitted light.

According to some embodiments of the invention, the light source transmits a broad bandwidth light. Optionally, the light source transmits a wavelength swept light.

According to some embodiments of the invention, the system further comprises a diffraction grating to spectrally disperse the illuminating light along an axis. Optionally, the system further comprises a collimator to collimate the illuminating light prior to spectrally dispersing the light.

According to some embodiments of the invention, the system further comprises a reference arm for creating interference between the emitted light and a reference light to determine axial location of the illuminated portion of the particle. Optionally, the acquired image is a three-dimensional (3-D) image of the illuminated portion of the particle. Optionally, the reference arm creates interference between the emitted light and the reference light to determine an axial component of a speed of the particle in the vessel.

According to some embodiments of the invention, the system comprises a single mode optical fiber for sending a single ray of illuminating light from the light source to the imaging probe. Optionally, the system comprises a multi-mode optical fiber for sending multiple rays of illuminating light from the light source to the imaging probe. Optionally, the system comprises a single mode optical fiber for carrying a single ray of emitted light from the imaging probe to the detection unit. Optionally, the system comprises a multi-mode optical fiber for carrying multiple rays of emitted light from the imaging probe to the detection unit.

According to some embodiments of the invention, the system comprises a dichroic mirror to collect the fluorescence into an optical fiber.

According to some embodiments of the invention, the system further comprises a display unit for displaying the acquired image.

According to some embodiments of the invention, the illuminated portion of the particle comprises a distinct spectral band.

According to some embodiments of the invention, a coherency between the emitted light and a reference light is not less than 1 μm and not greater than 10 mm.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF EMBODIMENTS OF THE INVENTION

Figure 1:
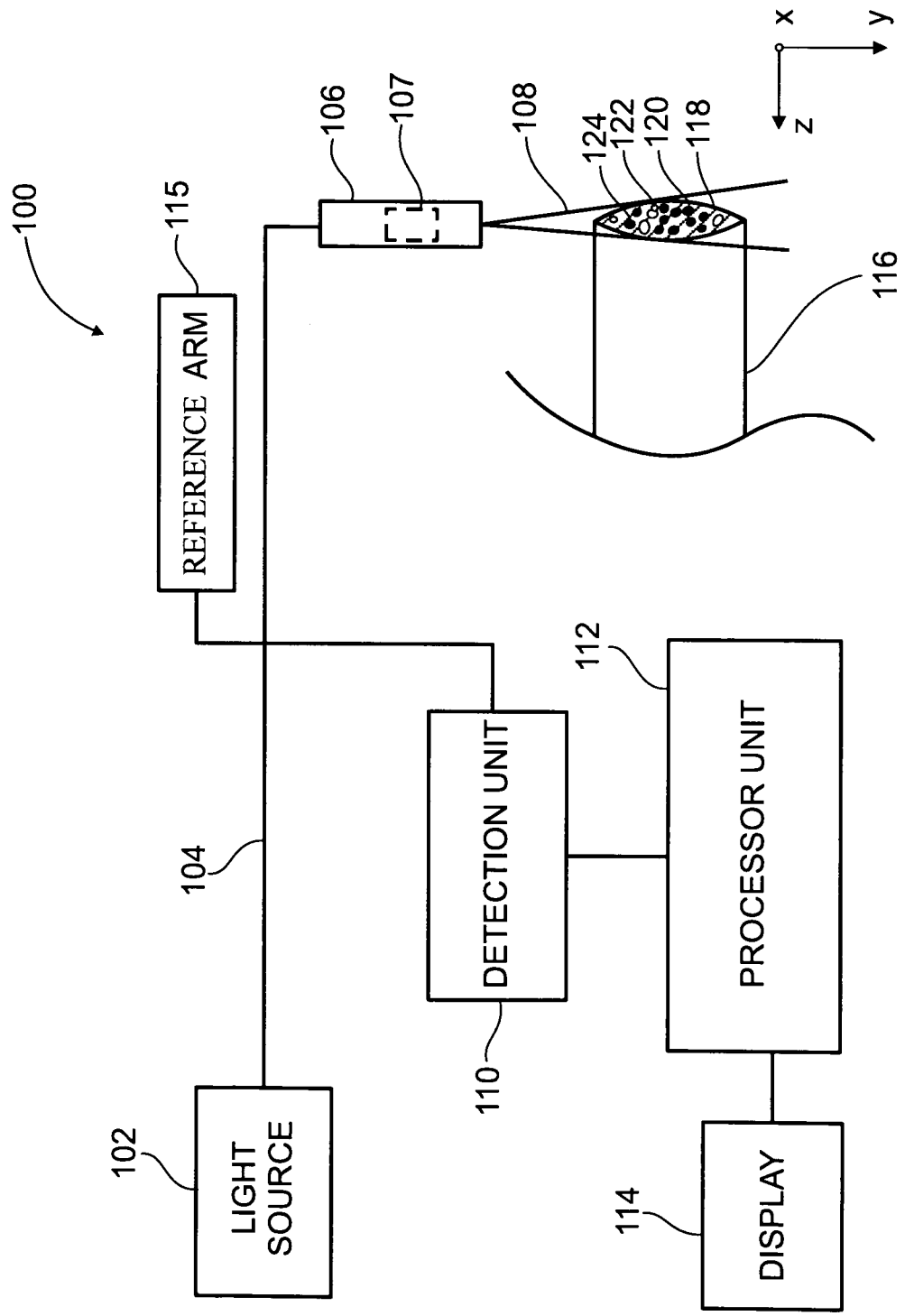
FIG. 1 schematically illustrates a functional block diagram of an exemplary system for imaging a vessel, in accordance with an embodiment of the present invention.

The present invention, in some embodiments thereof, relates to imaging devices and, more particularly, but not exclusively, to imaging systems and methods for medical and scientific applications.

An aspect of some embodiments of the present invention relates to a system and a method for acquiring an image of a particle (or more particles) flowing in a vessel by laterally statically illuminating at least a portion of the vessel with an illuminating light and reproducing the image of a portion of the particle(s) included in the illuminated portion of the vessel by detecting an emitted light produced by the particle(s) responsive to the illuminating light. As used herein, the term "laterally statically illuminating" refers to illuminating from a position external to the vessel with an imaging probe which does not include mechanical moving parts". For example, mechanical moving optical elements are not used. The illuminated light is spectrally dispersed along an axis of the portion of the vessel, and a spectrum of the emitted light is measured. The emitted light may include, but not be limited to, fluorescence, second harmonic generation, third harmonic generation, luminescence, Coherent anti-Stokes Raman scattering, Raman scattering, multi-photon fluorescence, phosphorescence, or any combination thereof. The method may include, but not be limited to, a use of a technique such as SEE. Optionally, SECM is used.

The reproduced image may be a cross-sectional 2D image, or optionally a 3D image, of the portion of the particle(s) included in the illuminated portion of the vessel. For convenience hereinafter, the term "portion of the particle(s) included in the illuminated portion of the vessel" may be interchangeably used with "illuminated particle" or "illuminated portion of the particle". The reproduced image may additionally comprise a cross-sectional 2D image, or optionally a 3D image, of the illuminated portion of the vessel. For convenience hereinafter, the term "illuminated portion of the vessel" may be interchangeably used with "illuminated vessel".

A further aspect of some embodiments of the present invention relates to performing in vivo, and optionally ex vivo, flow cytometry wherein a plurality of particles in the vessel may be substantially simultaneously counted and optionally examined based on the acquired image. The term "in vivo" as used herein in this disclosure, refers to inside a body, for example the body of a patient. The term "ex vivo", as used herein in this disclosure, refers to outside of the body, for example, as in vessels and/or organs externally connected to the body (optionally artificial), as in cultures, as in samples used in hydrodynamic-based flow cytometry, and/or as in blood samples extracted from the body. The system may determine a number of particles of different types in the vessel, and optionally, their location, speed of flow, size, length, shape, color, or brightness, or any combination thereof. These particles may include, but not be limited to, red blood cells, white blood cells, virus cells, amoeba, germ cells, bacteria, toxins, medicines, nano-particles, DNA, RNA, among other microscopic particles visible in light. The term "number" refers to a discrete quantity, and may optionally be a statistic or a relative number.

Current methods for detecting and quantifying various types of cells circulating within a blood stream typically involve extraction of blood from the subject (a patient or an animal) followed by labeling and ex vivo detection. For example, in standard flow cytometry, specific cell populations in a blood sample, drawn from a subject and fluorescently labeled, are passed in a flow stream to be interrogated by a light source (usually a laser). Fluorescence and light scattering signals emitted, or remitted, by the cells in response to the light source can be employed to determine the types and the number of the cells. These techniques suffer from a number of shortcomings. It is difficult to use these techniques to obtain a valid population profile for a cell type of interest that varies with time. These techniques can also suffer from a significant time delay between sample collection and analysis, leading to potential measurement inaccuracies.

Some in vivo techniques for detection of static and circulating fluorescently labeled cells are also known. However, these techniques typically show difficulty, or simply fail, in tracking cells flowing at a high velocity, especially in the arterial circulation, even when they capture images at video rates. In addition, employing these techniques for extracting quantitative information about the number and flow characteristics of a specific cell population can be very tedious.

In addition, conventional techniques for detecting and monitoring tumor progression and its response to available treatment modalities suffer from similar shortcomings. Methods such as histopathology and standard flow cytometry require taking tissue biopsies or blood samples from the patient. Further, some conventional non-invasive techniques, such as computed tomography, magnetic resonance imaging, and ultrasound, can typically detect only late-stage anatomical abnormalities.

Recently, confocal microscopy was demonstrated for in vivo flow cytometry, by using a slit confocal apparatus. While this technique allows fast acquisition times in vivo, cells are detected by their fluorescence signals and not through confocal imaging.

In an embodiment of the present invention, the system comprises a light source for generating the illuminating light; an imaging probe which may be an endoscope, optionally a catheter, for laterally illuminating the portion of the vessel and for capturing the emitted light from the illuminated particle; a detection unit for detecting the emitted light; a processing unit for reproducing the image of the illuminated particle, and optionally, of the illuminated vessel; and a display for displaying the 2D cross-sectional image of the illuminated particle and/or illuminated vessel, and optionally the 3D image. The processing unit additionally performs all computations associated with flow cytometry optionally displayed on the display.

The system may further include a reference arm for interferometry to improve signal-to-noise ratio (S/N) and to create interference between the emitted light and a low coherence reference light so that an axial location of the illuminated particle (for 3D imaging) may be determined. Coherency may range, for example, from 1 μm-10 mm, inclusively. Optionally, an axial component of a speed of the illuminated particle is determined. Optionally, Doppler imaging is used to determine the axial component of the speed.

In some embodiments of the present invention, the light source produces a broadband illuminating light. Optionally, the light source produces a varying wavelength (wavelength-swept) illuminating light. The illuminating light may comprise a wavelength in the range from 600 nm-1.3 μm. A potential advantage of using light of greater wavelength is a reduction in scattering and an increase in depth range.

In some embodiments of the present invention, the detection unit may include a spectrometer for measuring a distinct spectral band in the emitted light. Optionally, the detection unit is a CCD (charge-coupled device) camera for capturing a single shot of the emitted light. Optionally, the detection unit is a single detector for measuring a (discrete) wavelength of the emitted light.

In some embodiments of the present invention, the imaging probe is connected to the light source and to the detection unit through a single-mode optical fiber. Optionally, the connection is of the imaging probe to the light source is through a multi-mode optical fiber. Optionally, the connection of the imaging probe to the detection unit is through a multi-mode optical fiber.

In some embodiments of the present invention, broad bandwidth light is coupled to a fiber coupler, collimated, diffracted by a diffraction grating and focused onto a transverse line within the flow, where each resolvable point includes a limited range of wavelengths, optionally a single wavelength. Light that is scattered back from the focal line is collected by an objective lens, coupled back into the fiber, and then measured by a fast spectrometer. This optical configuration permits a single-shot line imaging, allowing fast confocal imaging across a vessel without any scanning mechanism.

In some embodiments of the present invention, low coherence interferometry is used to achieve depth information. By adding the reference arm, emitted light interferes with a reference light, which allow determining an axial location (along a z-axis) of the illuminated particle, as well as increase sensitivity and speed of the system. Using the coherence gate allows using a lower numerical-aperture lens which simplifies the system and provide larger depth range.

In some embodiments of the present invention, the system uses a rapid wavelength-swept source and a single photo detector. Potential advantages to this approach include simpler, more compact detection scheme that is less sensitive to misalignments, easier fluorescence detection, and/or more efficient signal collection using a double clad fiber or other incoherent waveguide.

In some embodiments of the present invention, the system includes separate illumination and emitting light collection channels. A single-mode fiber is optionally used for high-resolution illumination while a multimode fiber with larger core is optionally used to collect the backscattered and/or fluorescence light after passing through a beam splitter. This technique potentially improves one or more of signal efficiency, depth of field, speckle noise and reduces undesired back reflections from the optical setup. This configuration may also be useful for fluorescence detection, where the multimode fiber collects the fluorescence using a dichroic mirror instead of a beam splitter. A separation in space between the fluorescence and the excitation light is optionally provided and used to enable signal collection without a beam splitter.

A potential main benefit of spectrally encoded imaging for flow cytometry include imaging probes is that they are extremely compact and simple with no scanning or moving parts, and high spatial and temporal resolution imaging of the flowing particles or cells. The system can be constructed in a single unit using free-space optics or fiber optic, or in two units wherein one contains the light source, detection, analysis and display subsystems, and the other contains the compact probe with the distal optics. The two units are connected by only one or a few optical fibers. Potential applications include in vivo and ex vivo flow cytometry for industrial and for clinical applications. For in vivo applications, compactness of the probe, its simplicity, and its, lack of moving parts, may allow for performing endoscopic flow cytometry in various locations in the body. Exemplary dimensions for the imaging probe may be, but not be limited to, 20 mm×5 mm×5 mm; 15 mm×7 mm×5 mm; and 20 mm×6 mm×5 mm.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Referring now to the drawings, FIG. 1 schematically illustrates a functional block diagram of an exemplary system 100 for imaging a vessel 116, in accordance with an embodiment of the present invention. System 100 includes a light source 102, an imaging probe 106 including optical elements 107, a detection unit 110, a processor unit 112, and a display unit 114.

According to an embodiment of the present invention, system 100 acquires an image of one or more of a same type, or optionally a different type, of particles flowing in vessel 116, for example as shown by particles 120, 122 and 124 in body fluid 118, by laterally statically illuminating a portion of the vessel with an illuminating light 108 produced by light source 102, and detecting an emitted light (not shown) produced by the particles. Optionally, system 100 acquires an image of vessel 116. Optionally, system 100 includes a use of SEE. Optionally, system 100 includes a use of SECM. Particles 120-124 may include red blood cells, white blood cells, virus cells, amoeba, germ cells, bacteria, toxins, medicines, nano-particles, DNA, RNA, among other microscopic particle visible in lights. Vessel 116 may include veins, arteries, capillaries, artificial vessels, lymph, urinary tract, and other ducts internal, or optionally external, to the body and which may carry body fluids and particles.

Illuminating of the portion of vessel 116 may be performed by imaging probe 106, which may include for example, an endoscope, optionally a catheter. Illuminating light 108, which may include a broadband illuminating light or a wavelength-swept illuminating light, is guided from light source 102 to imaging probe 106 by an optical waveguide 104, which may include, for example a single optical fiber, or optionally, multiple optical fibers. Optical fiber 104 may be a single-mode optical fiber or optionally, a multi-mode optical fiber. Optionally, optical waveguide 104 may comprise reflecting mirrors and/or other optical elements suitable for directing light. Illuminating light 108 is spectrally dispersed along an x-axis and a y-axis of vessel 116 by optical elements 107 in imaging probe 106 which include a diffraction grating. Optionally, illuminating light 108 is spectrally dispersed along a z-axis. Illumination light 108 may comprise a wavelength in the range from 600 nm-1.3 µm. A potential advantage of using light of greater wavelength is a reduction in scattering and an increase in depth range.

Imaging probe 106 additionally collects the emitted light from particles 120-124, and optionally from vessel 116, and optically converts the emitted light using optical elements 107 for guiding to detection unit 110. The emitted light may include, but not be limited to, fluorescence, second harmonic generation, third harmonic generation, luminescence, Coherent anti-Stokes Raman scattering, Raman scattering, multiphoton fluorescence, phosphorescence, or any combination thereof. Optionally, capturing of emitted light is done by a second light capturing probe. Guiding of the emitted light from imaging probe 106 to detection unit 110 is done through optical fiber 104. Optionally, guiding is done through a second optical fiber, which may be a single-mode optical fiber, or optionally, a multi-mode optical fiber.

Emitted light captured by imaging probe 106 is detected by detection unit 110, and an output associated with a measure of a spectrum of the emitted light is generated for processing by processing unit 112. Detection unit 110 is selected according to the emitted light to be detected, and may include a spectrometer for measuring a distinct spectral band in the emitted light, a CCD camera for capturing a single shot of the emitted light, or a single detector for measuring a discrete wavelength of the emitted light, or any combination thereof. The emitted light may also be subject to low coherence interferometry with a reference light in reference arm 115 so that an axial (z-axis) location of particles 120-124 may be determined and used to obtain a 3D image. Optionally, an axial component of a speed of particles 120-124 is determined. Optionally, Doppler imaging is used to acquire the axial component of the speed of the particle.

According to an embodiment of the present invention, processing unit 112 processes the output from detection unit 110 and reproduces the acquired image of particles 120-124, and optionally vessel 116 and/or body fluid 118, for display on display unit 114. The reproduced image may be a cross-sectional 2D image along an x-axis and a y-axis, or optionally a 3D image (depth along a z-axis), of particles 120-124. The reproduced image may additionally comprise a cross-sectional 2D image, or optionally a 3D image, of the portion of vessel 116 and/or body fluid 118. Optionally, the reproduced image may include information related to the velocity of the particles.

According to an embodiment of the present invention, system 100 performs in vivo, and optionally ex vivo, flow cytometry. Based on the output of detection unit 110, processing unit 112 may simultaneously count, and optionally examine, particle 120-124, and may compute a number of particles of different types in vessel 116, and optionally, their location, speed of flow, length, shape, color, or brightness, or any combination thereof. The results of the computation may be displayed in display unit 114. Optionally, the results may be stored in magnetic media or other data storage means, printed, displayed by means other than display unit 114, or any combination thereof.

Figure 2:
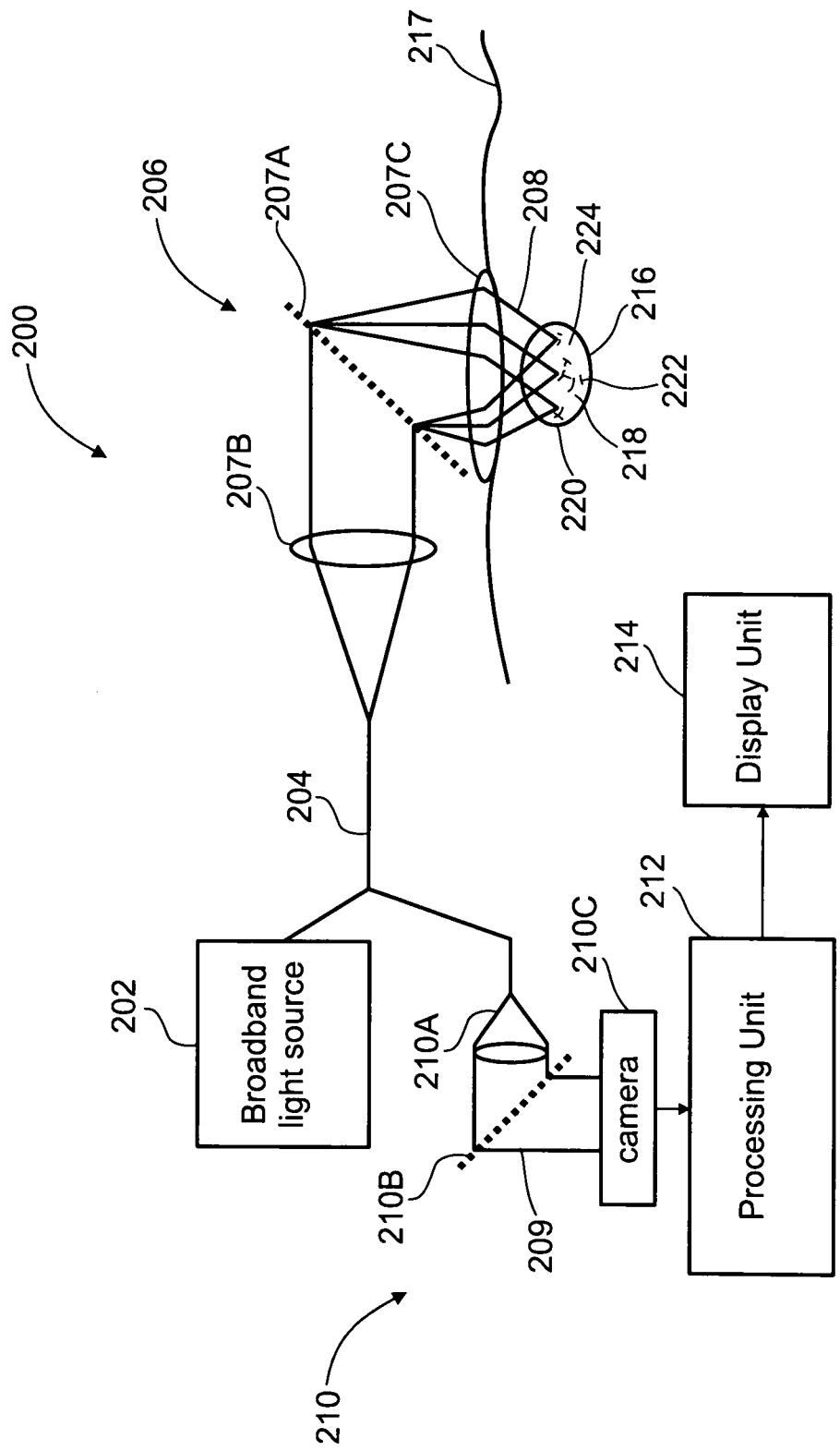
FIG. 2 schematically illustrates a functional block diagram of an exemplary system for imaging a vessel using a broadband light source, in accordance with some embodiments of the present invention.

Reference is made to FIG. 2 which schematically illustrates a functional block diagram of an exemplary system 200 for imaging a vessel 216 using a broadband light source 202, in accordance with some embodiments of the present invention. Vessel 216 is shown under tissue 217, and comprises body fluid 218 and particles 220, 222 and 224, which may be similar to that shown in FIG. 1 at 116, 118, 120, 122, and 124.

System 200, which may be similar to that shown in FIG. 1 at 100, comprises broadband light source 202 which may include a super-luminescent diode array; an optical waveguide 204 which may include an optical fiber; an imaging probe 206 including optical elements comprising a diffraction grating 207A for diffracting illuminating light 208, a collimator 207B for collimating the illuminating light, and a high NA focusing lens 207C for focusing the illuminating light; a spectrometer 210 including a CCD camera 210A, a collimator 210A for collimating an emitted light 209 and a diffraction grating 210B for diffracting the emitted light; a processing unit 212; and a display unit 214. Broadband light source 202; optical waveguide 204; imaging probe 206 including diffraction grating 207A, collimator 207B, and lens 207C; CCD camera 210 with collimator 210A and diffraction grating 210B; processing unit 212; and display unit 214; may be similar to that shown in FIG. 1 at 102, 104, 106 including 107, 110, 112, and 114.

According to some embodiments of the present invention, single-shot line imaging, and fast confocal imaging across vessel 216 is performed, without any scanning mechanism. Broad bandwidth illuminating light from light source 202 is coupled to optical fiber 204, collimated, spectrally diffracted and focused onto a transverse line (focal line) within a flow of body fluid 218 and particles 220-224 inside vessel 216, where each resolvable point on the line contains a single wavelength (each point is illuminated by a distinct spectral band). Emitted light 209 from each lines is collected by imaging probe 206, coupled back into fiber 204, and measured by fast spectrometer 210. An output of spectrometer 210 is processed by processing unit 212 and displayed on display unit 214.

Figure 3:
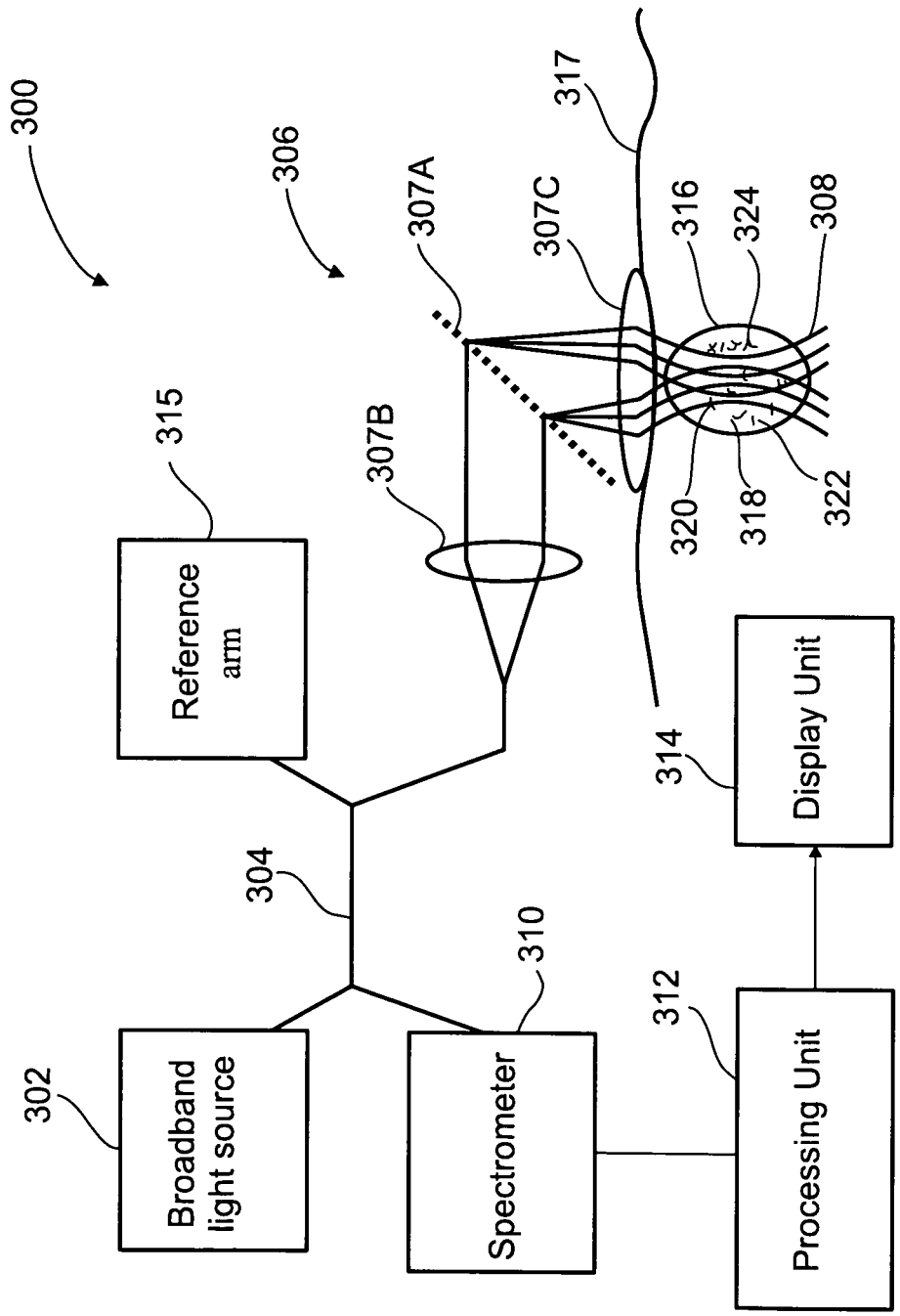
FIG. 3 schematically illustrates a functional block diagram of an exemplary system for imaging a vessel using a broadband light source and low coherence interferometry, in accordance with some embodiments of the present invention.

FIG. 3 schematically illustrates a functional block diagram of an exemplary system 300 for imaging a vessel 316 using a broadband light source 302 and a reference arm 315, in accordance with some embodiments of the present invention. Vessel 316 is shown under tissue 317, and comprises body fluid 318 and particles 320, 322 and 324, which may be similar to that shown in FIG. 1 at 116, 118, 120, 122, and 124.

System 300, which may be similar to that shown in FIG. 1 at 100, comprises broadband light source 302 which may include a super-luminescent diode array; an optical waveguide 304 which may include an optical fiber; an imaging probe 306 including optical elements comprising a diffraction grating 307A for diffracting illuminating light 308, a collimator 307B for collimating the illuminating light, and a focusing lens 307C for focusing the illuminating light; a spectrometer 310; a processing unit 312; a display unit 314; and reference arm 315. Broadband light source 302; optical waveguide 304; imaging probe 306 including diffraction grating 307A, collimator 307B, and lens 307C; spectrometer 310; processing unit 312; display unit 314; and reference arm 315; may be similar to that shown in FIG. 1 at 102, 104, 106 including 107, 110, 112, 114, and 115.

According to some embodiments of the present invention, low coherence interferometry in the range of 1 μm-10 mm, inclusively, is used to achieve depth information (3D topological information). The interferometry may be in the time domain and/or spectral domain. Reference arm 315, which may be included in a single-mode Michelson interferometer, creates interference between emitted light (not shown) from illuminated particles 320-324, and optionally from vessel 316 and/or body fluid 318, and a reference light, which allows for processing unit 312 determination of an axial (z-axis) location of the particles. Optionally, reference arm 315 may be included in a multi-mode Michelson interferometer. Optionally, reference arm 315 may be included in any other type of interferometer suitable for creating the interference. Optionally, system 300 sensitivity is increased. Optionally, system 300 imaging speed is increased. Optionally, a lower numerical aperture lens 307C may be used, reducing a complexity of system 300 and increasing a depth range. Optionally, Doppler imaging is used to determine the axial component of the velocity of the particle.

Broad bandwidth illuminating light from light source 302 is coupled to optical fiber 304, collimated, diffracted and focused within a flow of body fluid 318 and particles 320-324 inside vessel 316, where each resolvable point on the line contains a single wavelength. Emitted light 309 is collected by imaging probe 306, coupled back into fiber 304 and into reference arm 315, and measured by spectrometer 310. An output of spectrometer 310 is processed by processing unit 312 and displayed on display unit 314, and may include a 3D image or particles 320-324, vessel 316, or body fluid 318, or any combination thereof.

Figure 4:
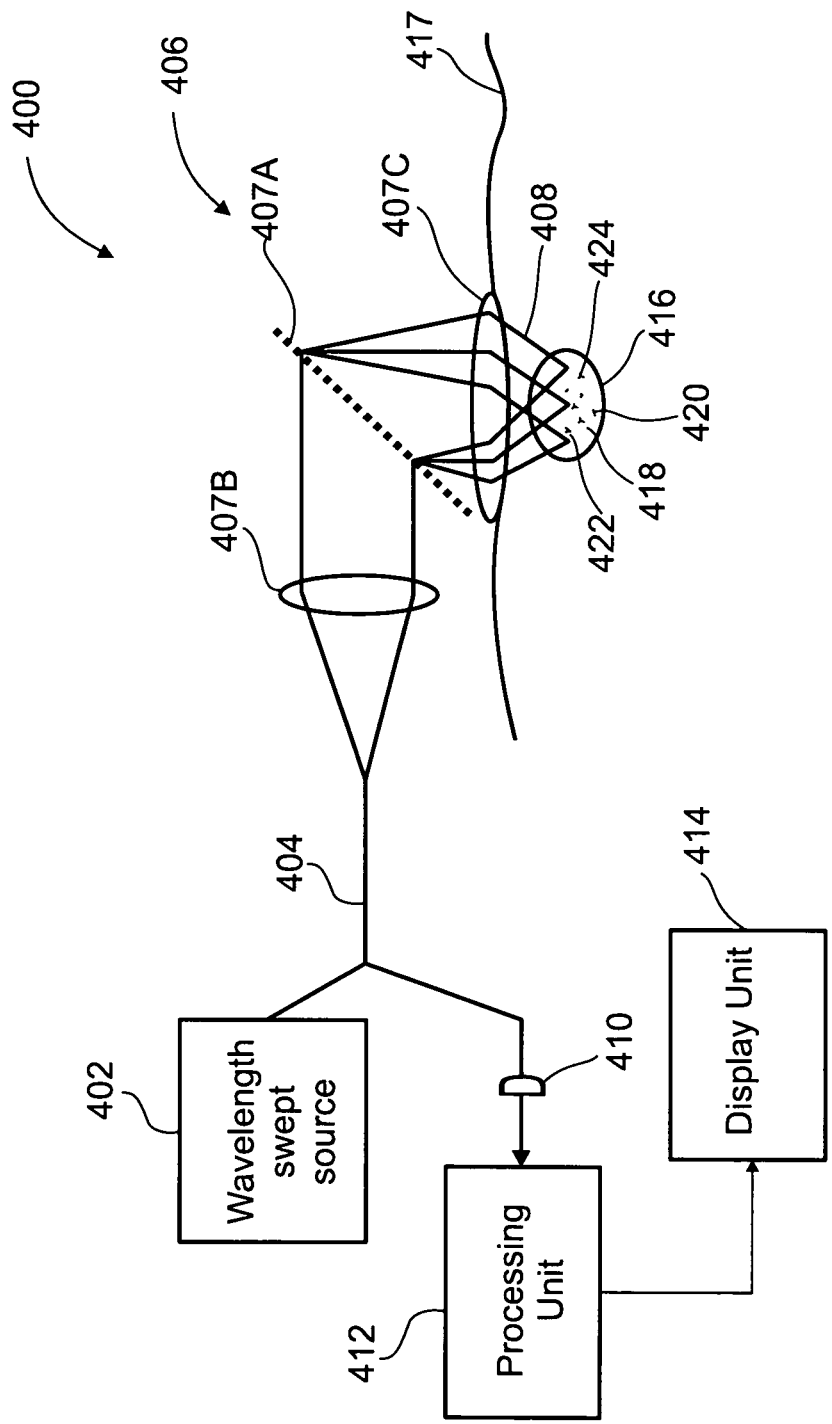
FIG. 4 schematically illustrates a functional block diagram of an exemplary system for imaging a vessel using a wavelength-swept light source, in accordance with some embodiments of the present invention.

FIG. 4 schematically illustrates a functional block diagram of an exemplary system 400 for imaging a vessel 416 using a wavelength-swept light source 402, in accordance with some embodiments of the present invention. Vessel 416 is shown under tissue 417, and comprises body fluid 418 and particles 420, 422 and 424, which may be similar to that shown in FIG. 1 at 116, 118, 120, 122, and 124.

System 400, which may be similar to that shown in FIG. 1 at 100, comprises a wavelength-swept light source 402 for producing illumination light of varying discrete wavelengths; an optical waveguide 404 which may include an optical fiber; an imaging probe 406 including optical elements comprising a diffraction grating 407A for diffracting illuminating light 408, a collimator 407B for collimating the illuminating light, and a focusing lens 407C for focusing the illuminating light; a detection unit 410 which may include a single-element photo detector; a processing unit 412; and a display unit 414. Wavelength-swept light source 402; optical waveguide 404; imaging probe 406 including diffraction grating 407A, collimator 407B, and lens 407C; photo detector 410; processing unit 412; and display unit 414; may be similar to that shown in FIG. 1 at 102, 104, 106 including 107, 110, 112, and 114.

According to some embodiments of the present invention, confocal imaging of a diffracted wavelength-swept illumination light 408 is done by relatively rapidly changing the wavelength of the light such that every point along a focal line in vessel 416 is illuminated (encoded) with a different wavelength while scanned one point at a time. By using point-by-point illumination, a need for spectral detection of the emitted light is eliminated and detection may be performed by a single-element photo detector 410.

Wavelength-swept illuminating light from light source 402 is coupled to optical fiber 404, collimated, diffracted and focused point-by-point within a flow of body fluid 418 and particles 420-424 inside vessel 416 such that each point is illuminated one-at-a-time by light of a single wavelength (by scanning one at a time). Emitted light 409 from each point in each line is collected one-by-one by imaging probe 406, coupled back into fiber 404, and measured by single-element photo detector 410. An output of photo detector 410 is processed by processing unit 412 and displayed on display unit 414.

Figure 5:
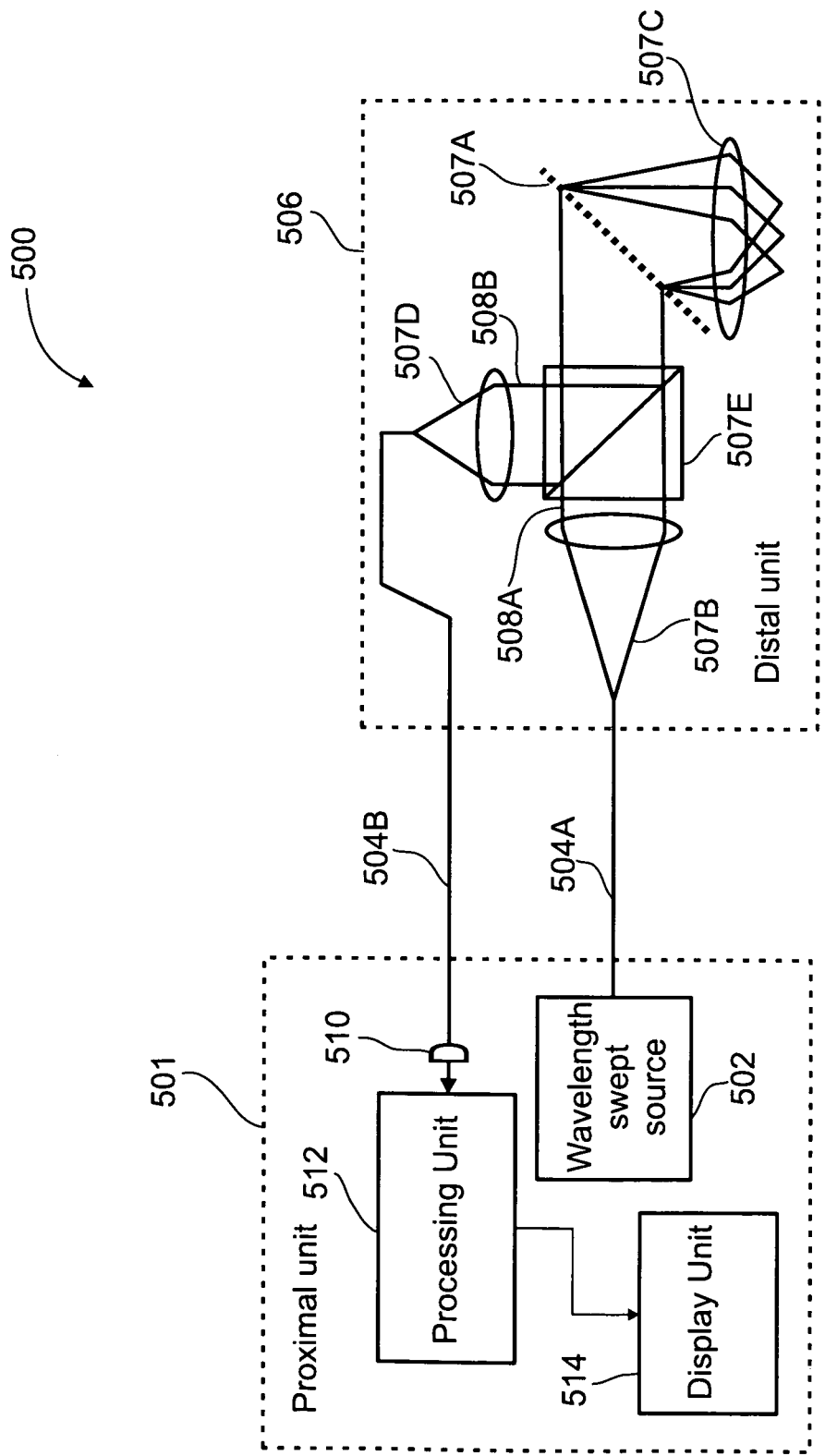
FIG. 5 schematically illustrates a functional block diagram of an exemplary system for imaging a vessel using a wavelength-swept light source, and single mode and multi-mode optical fibers including a beam splitter, in accordance with some embodiments of the present invention.

FIG. 5 schematically illustrates a functional block diagram of an exemplary system 500 for imaging a vessel (not shown) using a wavelength-swept light source 502, and a single-mode optical waveguide 504A and a multi-mode optical waveguide 504B for guiding an illumination light 508A and an emitting light 508B, respectively, in accordance with some embodiments of the present invention.

System 500, which may be similar to that shown in FIG. 1 at 100, comprises wavelength-swept light source 502 for producing illumination light of varying discrete wavelengths; single-mode optical waveguide 504A and multi-mode optical waveguide 504B which may each include an optical fiber; an imaging probe 506 including optical elements comprising a diffraction grating 507A for diffracting illuminating light 508A, a collimator 507B for collimating the illuminating light, a focusing lens 507C for focusing the illuminating light, a coupler 507D for coupling emitting light 508B to optical fiber 504B, and a beam splitter 507E for splitting the emitted light; a detection unit 510 which may be a single-element photo detector; a processing unit 512; and a display unit 514. Optionally, beam splitter 507E may be a dichroic mirror for fluorescence detection. Wavelength-swept light source 502; optical waveguides 504A and 504B; imaging probe 506 including diffraction grating 507A, collimator 507B, lens 507C, coupler 507D, and beam splitter 507E; photo detector 510, processing unit 512, and display unit 514, may be similar to that shown in FIG. 1 at 102, 104, 106 including 107, 110, 112, and 114.

System 500 is configured such that a proximal unit 501 includes light source 502, photo detector 510, processing unit 512, and display unit 514 with imaging probe (distal unit) 506 distally located. Connection of imaging probe 506 to proximal unit 501 is through optical fibers 504A and 504B.

According to some embodiments of the present invention, single-mode optical fiber 504A is used for high-resolution illumination while multi-mode optical fiber 504B with a larger core collects a backscattered/fluorescence emitted light 508B after passing through beam splitter 507E, optionally the dichroic mirror. Wavelength-swept illuminating light from light source 502 is coupled to optical fiber 504A, collimated, diffracted and focused onto a transverse line (focal line) in a vessel (not shown), where each resolvable point on the line contains a single wavelength (each point is illuminated by one by one by scanning one at a time). Emitted light 509 from each point in each line is collected one-by-one by imaging probe 506, split into separate beams by beam splitter 507E, optionally the dichroic mirror, and coupled into multi-mode optical fiber 504B. The beams are measured by single-element photo detector 510 and an output of the photo detector is processed by processing unit 512 and displayed on display unit 514.

Figure 6:
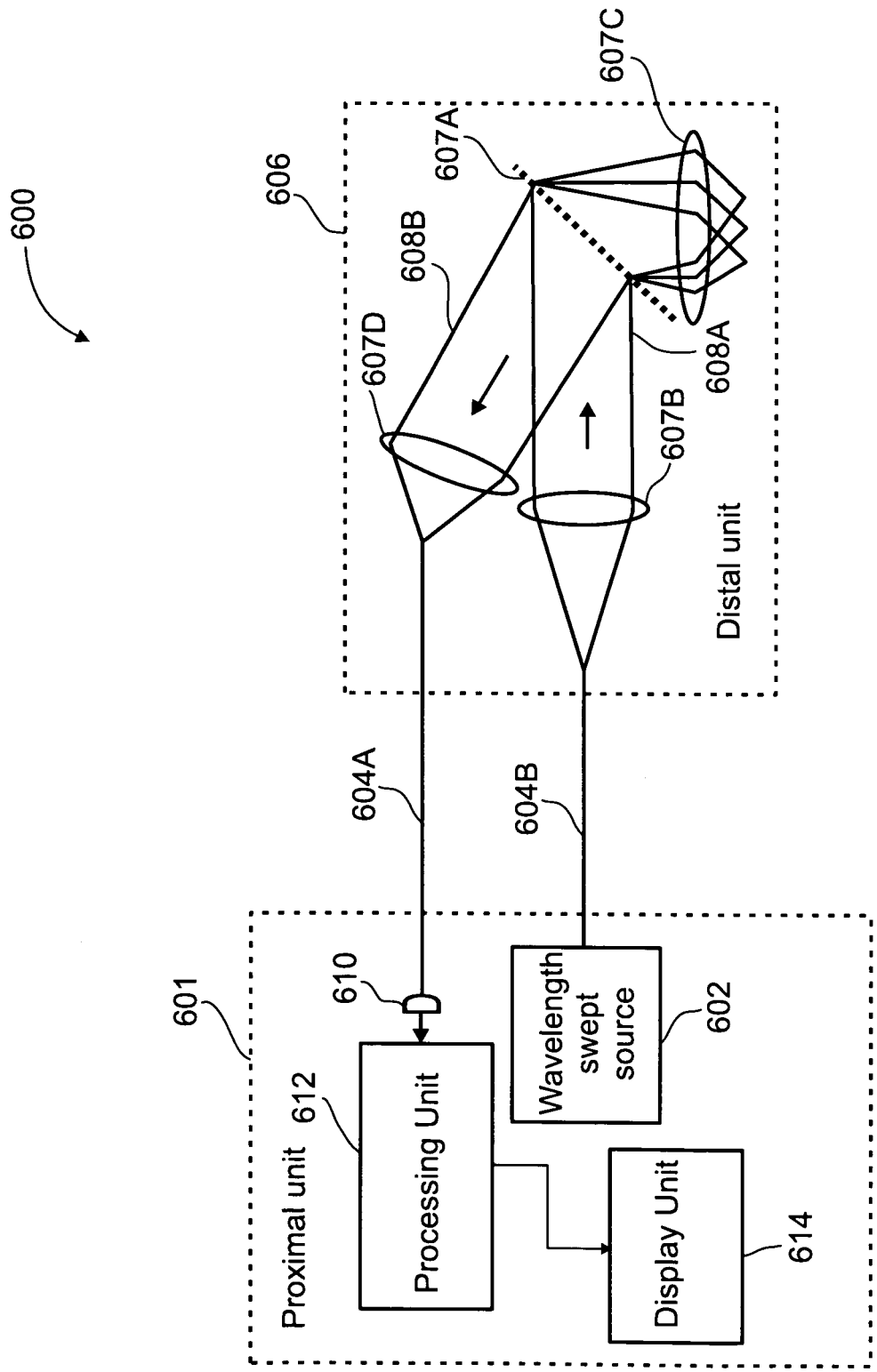
FIG. 6 schematically illustrates a functional block diagram of an exemplary system for imaging a vessel using a wavelength-swept light source and single mode and multi-mode optical fibers, in accordance with some embodiments of the present invention.

FIG. 6 schematically illustrates a functional block diagram of an exemplary system 600 for imaging a vessel (not shown) using a wavelength-swept light source 602, and a single-mode optical waveguide 604A and a multi-mode optical waveguide 604B for guiding an illumination light 608A and an emitting light 608B, respectively, in accordance with some embodiments of the present invention.

According to some embodiments of the present invention, spatially separating between fluorescence in the illuminated particle and/or illuminated vessel, and an illuminating light 608A, allows for using system 500 shown in FIG. 5 without a beam splitter. Therefore, system 600 may be similar to system 500 with the exception that the system does not include beam splitter 507E shown in FIG. 5.

System 600 comprises wavelength-swept light source 602 for producing illumination light of varying discrete wavelengths; single-mode optical waveguide 604A and multi-mode optical waveguide 604B which may each include an optical fiber; an imaging probe 606 including optical elements comprising a diffraction grating 607A for diffracting illuminating light 608A, a collimator 607B for collimating the illuminating light, a focusing lens 607C for focusing the illuminating light, and a coupler 607D for coupling emitting light 608B to optical fiber 604B; a detection unit 610 which may be a single-element photo detector; a processing unit 612; and a display unit 614. Wavelength-swept light source 602; optical waveguides 604A and 604B; imaging probe 606 including diffraction grating 607A, collimator 607B, lens 607C, and coupler 607D; photo detector 610, processing unit 612, and display unit 614, may be similar to that shown in FIG. 5 at 502; 504A; 504B; 506 including 507A, 507B, 507C, and 507D; 510, 512, and 514.

System 600 is configured such that a proximal unit 601 includes light source 602, photo detector 610, processing unit 612, and display unit 614 with imaging probe (distal unit) 606 distally located. Connection of imaging probe 606 to proximal unit 601 is through optical fibers 604A and 604B.

Figure 7B:
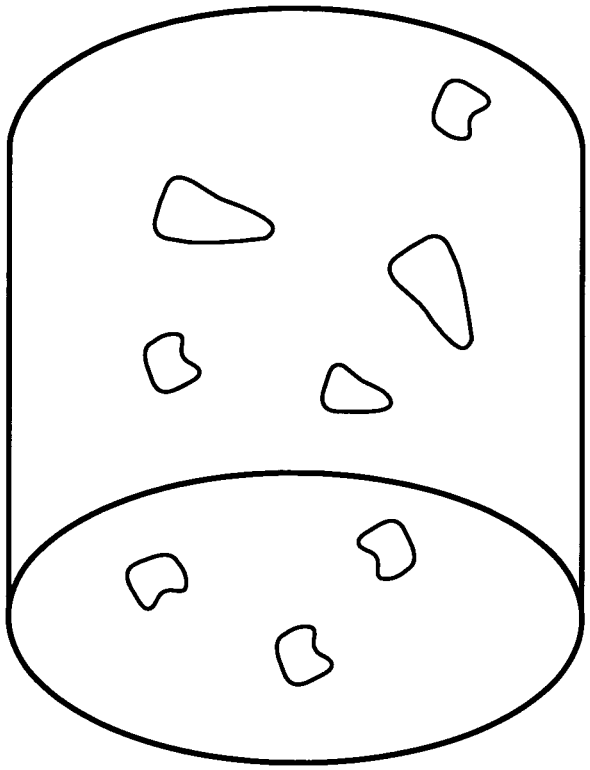
FIG. 7B schematically illustrates an exemplary cross-sectional image acquired by any exemplary system shown in FIGS. 1-6, in accordance with an embodiment of the present invention.
Figure 7A:
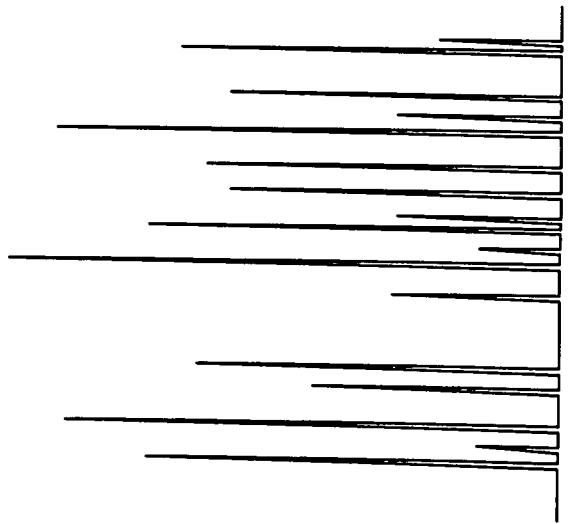
FIG. 7A schematically illustrates an exemplary single-event histogram from a cytometer, as known in the art.

Reference is made to FIG. 7A which schematically illustrates an exemplary single-event histogram from a cytometer, as known in the art, and to FIG. 7B which schematically illustrates an exemplary cross-sectional image along an x-axis and a y-axis of the of a vessel acquired by any one of system 100-600 shown in FIGS. 1-6, in accordance with an embodiment of the present invention. The single-event histogram shown in FIG. 7A is based on a use of a single laser beam aimed at a hydrodynamically-focused stream of fluid for counting particles one-by-one. From the cross-sectional image shown in FIG. 7B, additional information on particles aside from their number, such as for example, type, size, shape, location in the vessel, color, brightness, and the like, may be readily obtained. The additional information may be used to increase the speed of measurement by increasing the flow rate, its accuracy, and for the implementation of new cell collection systems that may use this information for more efficient and accurate cell sorting.

Figure 8:
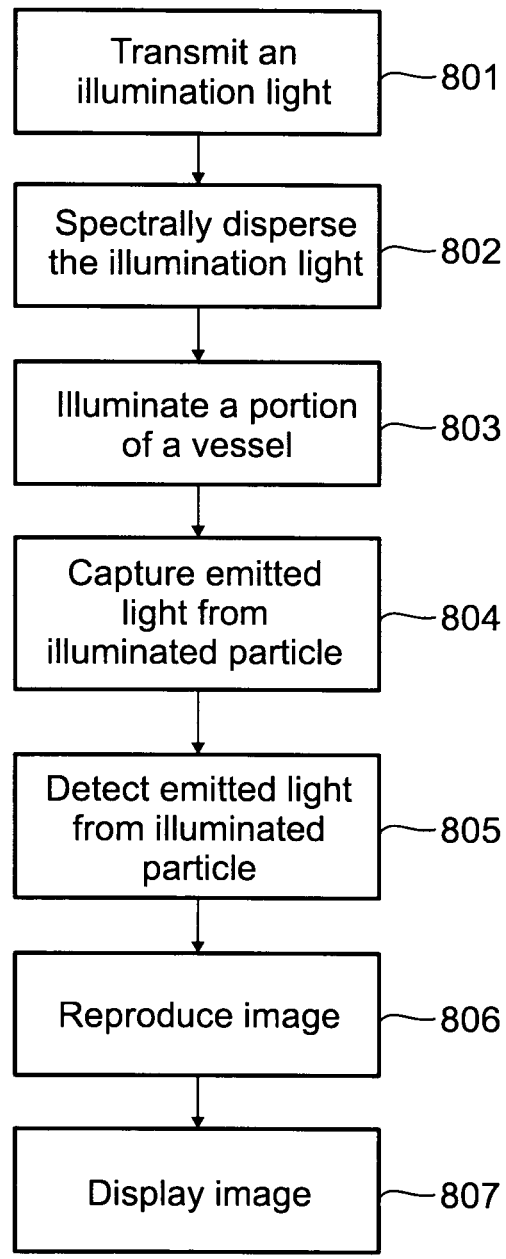
FIG. 8 illustrates a flow chart of a method for acquiring an image of a particle in a vessel, in accordance with an embodiment of the present invention.

Reference is made to FIG. 8 which illustrates a flow chart of an exemplary method for acquiring an image of a particle in a vessel, in accordance with an embodiment of the present invention. Reference is also made to FIG. 1. It should be evident to a person skilled in the art that the exemplary method described herein may be implemented in other ways, forms, and/or manners, and is therefore not intended to be limiting to the method described.

At 801, illumination light 108 is produced by light source 102 and sent over optical waveguide 104 to imaging probe 106 which may include an endoscope or a catheter. Illumination light 108 may be a broadband light or a wavelength-swept light. Optical waveguide 104 may be a single-mode optical fiber. Optionally, waveguide 104 may be a multi-mode optical fiber.

At 802, illumination light 108 is received by imaging probe 106 where the light is collimated by a collimator and spectrally diffracted by a diffracted grating in optical element 107. Optionally, illumination light 108 is not collimated.

At 803, a portion of vessel 116 is illuminated by illumination light 108, the light spectrally dispersed along the x-axis of the vessel.

At 804, particles 120-124, and optionally illuminated vessel 116 and/or body fluids 118, produce emitted light responsive to being illuminated by illumination light 108. Imaging probe 106 collects (captures) the emitted light which is optically processed by optical element 107 for sending through optical fiber 104 to detection unit 110. Optionally, the emitted light may be sent to reference arm 115 for creating an interference with a reference low coherency light for obtaining axial information (along a z-axis) on the illuminated particle 120-124 and/or illuminated vessel 116, for reproduction of a 3D image. Optionally, the axial component of the speed of the particle is determined.

At 805, emitted light is detected by detection unit 110. Detection unit 110 may include a spectrometer for measuring a distinct spectral band in the emitted light, a CCD camera for capturing a single-shot image of the emitted light, a single-element photo detector for measuring a discrete wavelength of the emitted light, or any combination thereof. Detection unit 110 generates an output to processing unit 112 based on the measurements.

At 806, processing unit 112 processes the output received from detection unit 110 and reproduces the image of illuminated particle 120-124 and/or illuminated vessel 116. Processing unit 112 performs all computations associated with flow cytometry, including substantially simultaneous determination of a number of particles, and other characteristics such as their type, size, shape, color, brightness, and the like.

At 807, display unit 114 displays information from processing unit 112. The information may be the 2D cross-sectional image of illuminated particle 120-124, illuminated vessel 116, body fluid 118, or any combination thereof, and optionally the 3D image. Optionally, flow cytometry information computed by processing unit 112 is displayed.

It is expected that during the life of a patent maturing from this application many relevant systems and/or methods will be developed and the scope of the term system and/or method is intended to include all such new technologies a prior.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method for acquiring at least one of a two-dimensional (2D) cross-sectional image and a three-dimensional (3D) image of at least a portion within a vessel, the image including an image of a particle flowing in the vessel, the method comprising:

illuminating, using an imaging probe having an axis of illumination, at least a portion within said vessel with an illuminating light, wherein said illuminating includes diffracting the illuminating light and then focusing the illuminating light onto a transverse line within a flow within the vessel;

detecting emitted light from an illuminated portion of said particle within the vessel; and reproducing an image of the illuminated portion of said particle within the vessel from the emitted light, wherein the reproduced image is at least one of a two-dimensional (2D) cross-sectional image and a three-dimensional (3D) image, and wherein one of the dimensions of the reproduced image is along the illumination axis.

2. The method of claim 1, comprising acquiring an image of a cross-section of the portion of the vessel.

3. The method of claim 2 wherein the image of the cross-section of the vessel comprises a cross-section of one or more particles in the portion of the vessel.

4. The method of claim 1 further comprising spectrally dispersing the illuminating light along the axis.

5. The method of claim 1 further comprising collimating the illuminating light prior to spectrally dispersing the light.

6. The method of claim 1 wherein the illuminated portion of said particle comprises a distinct spectral band.

7. The method of claim 1 wherein detecting light from the illuminated portion of said particle comprises measuring a spectrum of the emitted light.

8. The method of claim 1 further comprising creating interference between the emitted light and a reference light to determine axial location of the illuminated portion of said particle.

9. The method of claim 8 comprising reproducing a three-dimensional (3-D) image of the illuminated portion of said particle.

10. The method of claim 1 further comprising creating interference between the emitted light and a reference light to determine an axial component of a speed of the particle in said vessel.

11. The method of claim 1 further comprising sending the illuminating light through a single mode optical fiber and/or a multi-mode optical fiber.

12. The method of claim 1 further comprising receiving the emitted light through a single mode optical fiber and/or a multi-mode optical fiber.

13. The method of claim 1 wherein the illuminating light is a broad bandwidth light or a wavelength-swept light.

14. The method of claim 1 further comprising counting a number of particles in said vessel.

15. The method of claim 1 further comprising determining a location, a speed of flow, an axial component of a speed of flow, a size, a length, a shape, a color, or a brightness of a particle, or any combination thereof, in said vessel.

16. The method of claim 1 comprising acquiring the image of said particle in-vivo and/or ex-vivo.

17. The method of claim 1 wherein detecting emitted light comprises detecting fluorescence, second harmonic generation, third harmonic generation, luminescence, Coherent anti-Stokes Raman scattering, Raman scattering, multi-photon fluorescence, or phosphorescence, or any combination thereof.

18. The method of claim 1, further comprising acquiring a two-dimensional (2D) image of an additional particle flowing in the vessel, the additional particle is of a different type from that of the particle.

19. The method of claim 1, wherein said illuminating comprises non-scanning illumination.

20. The method of claim 1, wherein said illuminating is performed without mechanical moving parts.

21. The method of claim 1, further comprising determining a number of particles of different types in said vessel.

22. The method of claim 19, wherein said determining includes determining a discrete quantity of particles of different types in said vessel.

23. The method of claim 1, further including determining an axial location of said particle.

24. The method of claim 1, wherein said reproducing includes reproducing an image of the illuminated portion of an individual particle.

25. The method of claim 1, further comprising determining a type of the particle.

26. The method of claim 1, wherein the illuminating light is focused with a high NA lens.

27. The method of claim 1, wherein said reproducing an image includes reproducing a 3D image of the particle, the 3D image having a depth dimension.

28. The method of claim 1, wherein said reproducing an image includes processing the detected emitted light from the illuminated portion of the particle within the vessel to determine a location, a speed of flow, an axial component of a speed of flow, a size, a length, a shape, or any combination thereof of the particle.

29. A system for acquiring at least one of a two-dimensional (2D) cross-sectional image and a three-dimensional (3D) image of at least a portion within a vessel, the image including an image of a particle flowing in the vessel, the system comprising:
a light source for generating an illuminating light, wherein said illuminating light is diffracted and then focused onto a transverse line within a flow within the vessel;
an imaging probe for illuminating at least a portion within said vessel along an axis with the illuminating light;
a detection unit for detecting emitted light from an illuminated portion of said particle within the vessel; and
a processor unit for reproducing an image of the illuminated portion of said particle within the vessel from the emitted light, wherein the reproduced image is at least one of a two-dimensional (2D) cross-sectional image and a three-dimensional (3D) image, and wherein one of the dimensions of the reproduced image is along the illumination axis.

30. The system of claim 29 wherein the imaging probe captures the emitted light from the illuminated portion of said particle.

31. The system of claim 29 wherein the imaging probe is an endoscope.

32. The system of claim 29 wherein the imaging probe is a catheter.

33. The system of claim 29 wherein the processor unit reproduces an image of a cross-section of the portion of the vessel.

34. The system of claim 29 wherein the image of the cross-section of the portion of the vessel comprises a cross-section of one or more particles in the portion of the vessel.

35. The system of claim 29 wherein the detection unit comprises a spectrometer for measuring a spectrum of the emitted light, a camera for capturing a single shot of the emitted light, or a single detector for measuring a wavelength of the emitted light, or any combination thereof.

36. The system of claim 29 further comprising a diffraction grating to spectrally disperse the illuminating light along the axis.

37. The system of claim 29 wherein the illuminated portion of said particle comprises a distinct spectral band.

38. The system of claim 29 further comprising a reference arm for creating interference between the emitted light and a reference light to determine axial location of the illuminated portion of said particle.

39. The system of claim 29 wherein the acquired image is a three-dimensional (3-D) image of the illuminated portion of said particle.

40. The system of claim 29 further comprising a reference arm for creating interference between the emitted light and a reference light to determine an axial component of a speed of the particle in said vessel.

41. The system of claim 29 further comprising a single-mode optical fiber and/or multi-mode optical fiber for sending multiple rays of illuminating light from the light source to the imaging probe.

42. The system of claim 29 further comprising a single-mode optical fiber and/or a multi-mode optical fiber for carrying multiple rays of emitted light from the imaging probe to the detection unit.

43. The system of claim 29 wherein the light source transmits a broad bandwidth light and/or a wavelength swept light.

44. The system of claim 29 wherein the processor unit counts a number of particles in said vessel.

45. The system of claim 29 wherein the processor unit determines a location, a speed of flow, a size, a length, a shape, a color, or a brightness of a particle, or any combination thereof, in said vessel.

46. The system of claim 29 wherein the imaging probe illuminates a portion of said particle in-vivo and/or ex-vivo.

47. The system of claim 29 wherein the detection unit detects fluorescence, second harmonic generation, third harmonic generation, luminescence, Coherent anti-Stokes Raman scattering, Raman scattering, multi-photon fluorescence, or phosphorescence, or any combination thereof.

48. The System of claim 29, wherein said imaging probe is configured to illuminate at least a portion within the vessel using one of a broadband illuminating light and a light source producing a varying wavelength illuminating light.

49. The system of claim 29, wherein said imaging probe does not include mechanical moving parts.

* * * * *